United States Patent [19]

Odake et al.

[11] Patent Number: 5,001,353
[45] Date of Patent: Mar. 19, 1991

[54] METHOD AND APPARATUS TO MEASURE THE THICKNESS OF COATING FILMS

[75] Inventors: Atushi Odake; Nobuyuki Takahashi, both of Nagoya, Japan

[73] Assignee: Sumitomo Light Metal Industries, Ltd., Tokyo, Japan

[21] Appl. No.: 464,304

[22] Filed: Jan. 12, 1990

[30] Foreign Application Priority Data

Jan. 17, 1989 [JP] Japan .................................. 1-8298

[51] Int. Cl.$^5$ ............................................ G01N 21/64
[52] U.S. Cl. .................................. 250/461.1; 250/372; 250/459.1
[58] Field of Search ............... 250/461.1, 458.1, 459.1, 250/372

[56] References Cited

U.S. PATENT DOCUMENTS

| | | | |
|---|---|---|---|
| 3,663,813 | 5/1972 | Shaw | 250/461.1 |
| 3,956,630 | 5/1976 | Mellows | 250/461.1 |
| 4,841,156 | 6/1989 | May et al. | 250/461.1 |
| 4,899,055 | 2/1990 | Adams | 250/372 |
| 4,906,100 | 3/1990 | Rice et al. | 356/417 |
| 4,916,319 | 4/1990 | Telfair et al. | 250/461.1 |
| 4,922,113 | 5/1990 | Melancon | 250/372 |

Primary Examiner—Constantine Hannaher
Assistant Examiner—Edward J. Glick
Attorney, Agent, or Firm—Flynn, Thiel, Boutell & Tanis

[57] ABSTRACT

This invention provides a method and apparatus to measure the thickness of coating films on running metal sheets to which oil or paint is applied forming coating film such as oil film or paint film. The method to measure coating film thickness employed by this invention is carried out as follows: ultraviolet radiation is projected onto the film formed on the metal sheet; fluorescence emitted due to excitation is detected by a high-sensitivity TV camera; the signal representing the intensity of detected fluorescence is amplified; and the quantity of coating such as oil or paint on the sheet is obtained from the intensity of the amplified signal, which is processed to correct the linear relation between the quantity of coating and the intensity of fluorescence. This invention enables accurate measurement of thickness of coating film such as oil film or paint film coated on metal sheet in an on-line system.

7 Claims, 5 Drawing Sheets

1 ULTRAVIOLET RAY RADIATION LAMP FOR EXCITATION
2 HIGH-SENSITIVE TV CAMERA
10 SHEET
6 TV CAMERA CONTROLLER
3 IMAGE PROCESSING DEVICE
4 DISPLAY DEVICE OF OPERATION

METHOD AND APPARATUS TO MEASURE THE THICKNESS OF COATING FILMS

FIELD OF THE INVENTION

This invention relates to a method and apparatus for measuring the thickness of coating film. Particularly, this invention refers to a method and apparatus for measuring the thickness of oil films or paint films formed on running sheet metal to which oil or paint is applied.

This invention constitutes an on-line method and apparatus for the real-time measurement of the thickness or quantity of oil films or paint films coated on rolled sheet metals, such as aluminum sheet for can material.

BACKGROUND OF THE INVENTION

Oil is coated on rolled metal sheets, e.g. aluminum for can material or other sheet metals, to provide auxiliary lubrication during the press forming process. This operation is called reoiling, and has conventionally been carried out by continuously spraying oil over the entire surface of the running sheet. Non-uniformity of oil films formed on sheets can cause defects in quality, such as black streaks, so the measurement of quantity or thickness of the oil film has become a very important factor in the control of the manufacturing process.

In the past, measurement of oil film thickness was carried out using the following methods: measuring the weight difference of a test piece before and after the removal of oil film; the FT - IR method whereby the amount of infrared ray absorbed by the oil film surface is measured; and the atmospheric-type ultraviolet photoelectron detection method whereby ultraviolet rays are applied to a test piece and photoelectron emissions are measured.

Measuring of the thickness of paint film coated on rolled metal sheet was carried out using the following methods: the infrared ray absorption method whereby the characteristic of absorbing a definite range of infrared ray wave length of coated paint is utilized; and the $\beta$ ray diffusion method whereby $\beta$ ray is applied to the paint film and the amount of $\beta$ ray diffused or scattered by the paint film is measured because the amount of $\beta$ ray diffusion is closely connected with the thickness of paint film.

The above-mentioned off-line oil film measuring methods, however, do not permit assessment of the entire length and width of the sheet, because only locally sampled test pieces are examined. In addition, the weight or FT - IR methods are burdened by the considerable time and effort needed for the preparation of measurements; and the atmospheric-type photoelectron detection method by ultraviolet ray is limited by the thinness of the oil film when measuring.

The problem of the above paint film thickness measuring methods is the inferiority in measuring accuracy. And another problem is that the measuring place on the paint film is very limited spot. It also results in inaccurate measurement.

SUMMARY OF THE INVENTION

This invention has been developed on the basis that fluorescent phenomena detected on coating film such as oil films or paint films following ultraviolet ray radiation can be effectively used for determination of coating film thickness, and that concrete techniques for measurement have been investigated. The main object of this invention is to provide a novel, on-line method and apparatus to perform real-time measurements of coating film conditions over the entire surface of a sheet.

In order to achieve the above-mentioned purpose, the on-line measurement of coating film thickness performed by this invention consists of directing ultraviolet radiation onto the film coated on a running sheet surface; and then measuring the intensity of fluorescence emitted due to excitation as detected by a high-sensitivity TV camera. Finally, the quantity and thickness of the film is converted to signal strength by an image processing device.

The apparatus of this invention for on-line measurement of coating film such as oil film or paint film consists mainly of the following: an ultraviolet lamp to irradiate the surface of the sheet and excite particles; a high-sensitivity TV camera set at an angle of 90° or less to the axis of ultraviolet irradiation projected from the overhead ultraviolet lamp; and an image processing device and display device of operation which are directly connected to the high-sensitivity camera.

In using this apparatus and method, it is preferable to spectroscopically analyze the ultraviolet ray to be radiated onto the coating film into arbitrary wavelengths from 200 to 400 nm. It is also important to select a high-sensitivity camera having optimum performance in the range (400 to 500 nm) of fluorescence to be emitted.

This invention is constructed so that ultraviolet rays radiated onto the coating film coated on sheets will induce emission of fluorescence due to excitation of particles in the oil or paint on the sheet. The intensity of this fluorescence has a definite functional relation to the thickness of the oil or paint film. Thus, when the fluorescence is detected by a high-sensitivity TV camera, and the input signal is amplified, corrected, and passed through an image processing device, the quantity and thickness of the film can be displayed on a suitable display device.

This measuring mechanism makes it possible to measure coating film such as oil film or paint film over the entire surface of sheet-type material while it is running on a continuous process, thus making real-time on-line measurement, with high precision, a reality.

BRIEF DESCRIPTION OF THE DRAWINGS

FIG. 6 depicts an obtained chart with no oil coating, FIG. 7 shows conditions when 200 mg/m$^2$ of oil is coated, and FIG. 8 shows conditions obtained when 400 mg/m$^2$ of oil coated.

DETAILED DESCRIPTION OF THE PREFERRED EMBODIMENT

The following description of this invention is based on real implementation.

Figure 1:
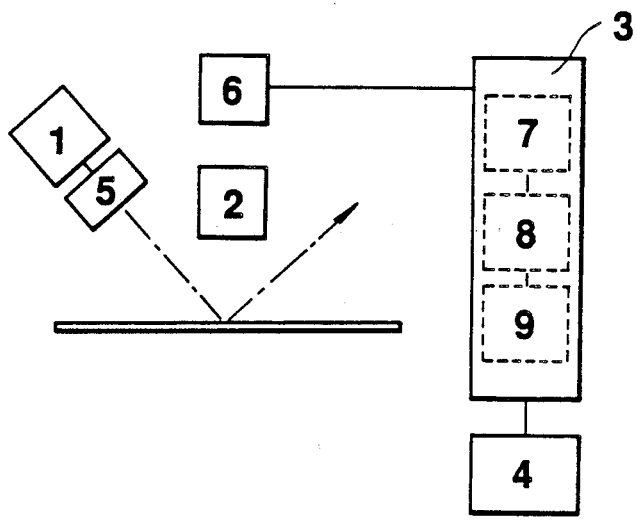
FIG. 1 is a block diagram showing the structure of the on-line measuring apparatus relating to this invention.
Figure 2:
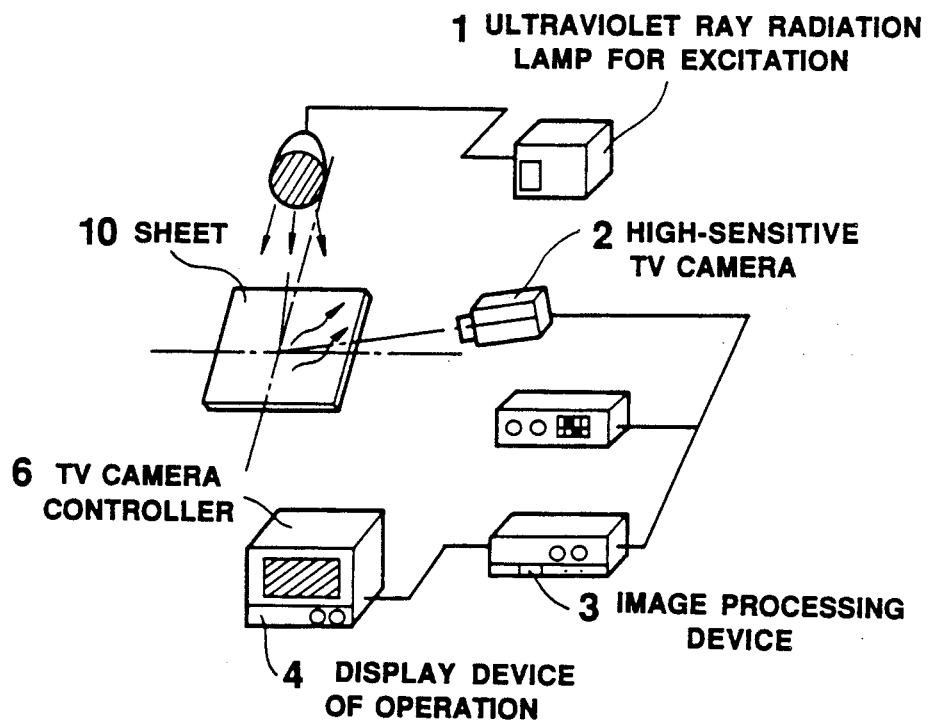
FIG. 2 is an oblique drawing showing the arrangement of apparatuses and materials.

FIG. 1 is a block diagram showing the structure of the on-line measuring apparatus relating to this invention. FIG. 2 is an oblique illustration of the arrangement. In these drawings, (1) is an ultraviolet radiation lamp for excitation, (2) is a high-sensitivity TV camera, (3) is an image processing device and (4) is a display device of operation.

Figure 3:
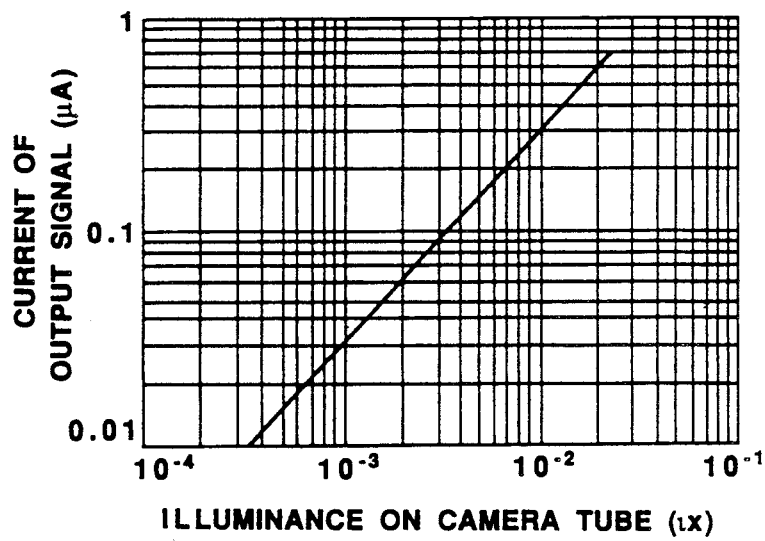
FIG. 3 is a photoelectrical conversion characteristic diagram of a camera tube which works effectively as the ultraviolet ray radiation lamp for excitation.
Figure 4:
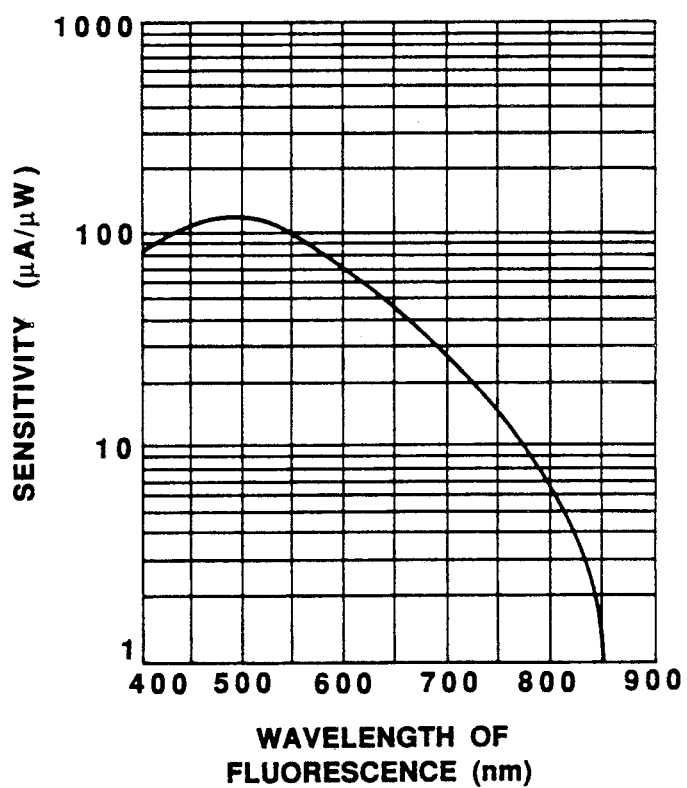
FIG. 4 is a diagram showing spectroscopic sensitivity.

The high-sensitivity camera performs as shown in the photoelectrical conversion characteristic diagram of a camera tube depicted in FIG. 3 and in the diagram showing spectroscopic sensitivity in FIG. 4. Generally, a spectroscope (5) which adjusts the ultraviolet wavelength to within the range of 200 to 400 nm, is attached in front of the lamp, and a TV camera controller (6) is installed to control the camera set.

The image processing device (3) is composed of an integrating circuit (7) for amplifying the signal received by the high-sensitivity TV camera, a background noise reducing unit (8) to eliminate the distributive influence of ultraviolet radiation, and a linearizer unit (9) to correct the linear relation between the quantity of oil or paint and the strength of fluorescence.

Figure 5:
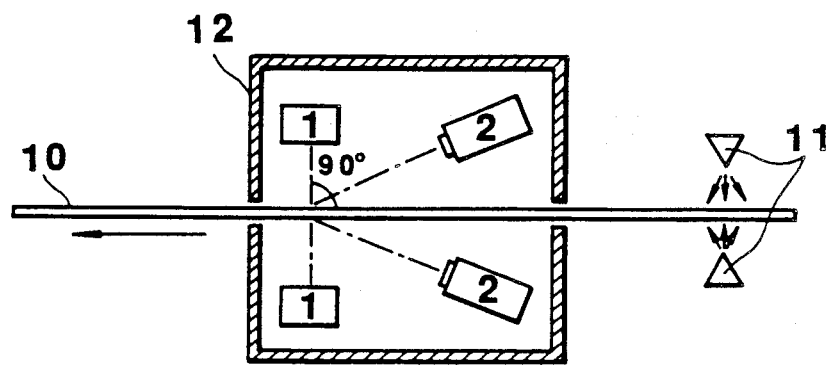
FIG. 5 shows a cross-sectional view of the installed apparatus used in this invention.

As shown in the cross-sectional view of the installed apparatus in FIG. 5, the ultraviolet radiation lamp for excitation (1) and the high-sensitivity TV camera (2) are both housed as one unit in a dark room (12) into which the sheet (10) enters after passing through an oil spraying unit (11). The UV projection and reception devices unit should be fixed so that the angle between the axis of the high-sensitivity TV camera and the axis of projection of ultraviolet rays radiated from the ultraviolet ray radiation lamp for excitation is 90° or less. This specific arrangement is to prevent errors caused by direct incidence of light from the ultraviolet ray radiation lamp into the TV camera, and it is best to either arrange them at right angles or to align the radiating-light unit and receiving-light unit in the same direction.

The above-mentioned apparatus was set up on an aluminum can-material process line, and the oil film coated on running sheets was measured before and after the application of oil spray. In this case, the arrangement of the light radiation and light receiving units was as follows: the ultraviolet radiation lamp for excitation (1) was set perpendicular to the running line of the sheet, and at a 45° angle 200 mm above the sheet; the high-sensitivity TV camera (2) was set at a 35° light-receiving angle such that the angle between the camera axis and radiation axis of the overhead ultraviolet lamp is 90°, and at a distance of 250 mm from the lamp.

Figure 6:
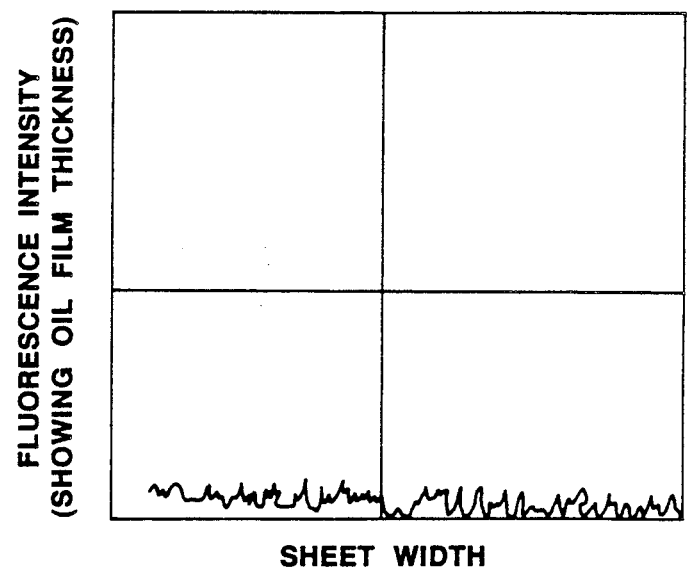
FIGS. 6 to 8 show the display of a signal output from oil film. Specifically.
Figure 7:
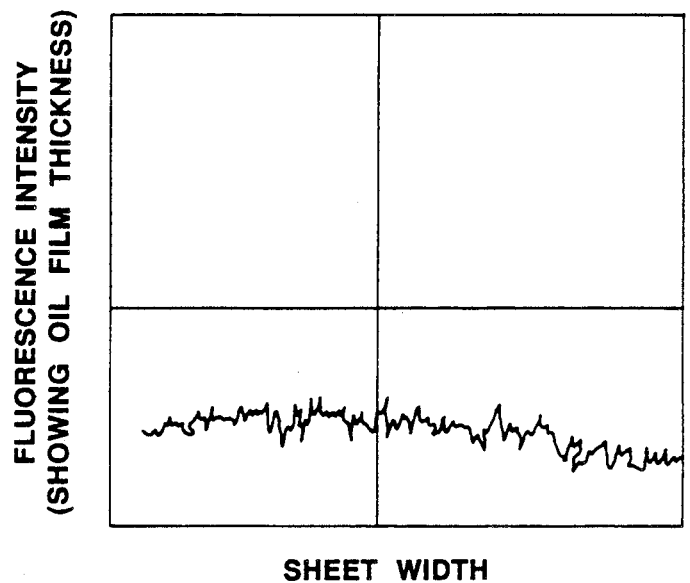
Figure 8:
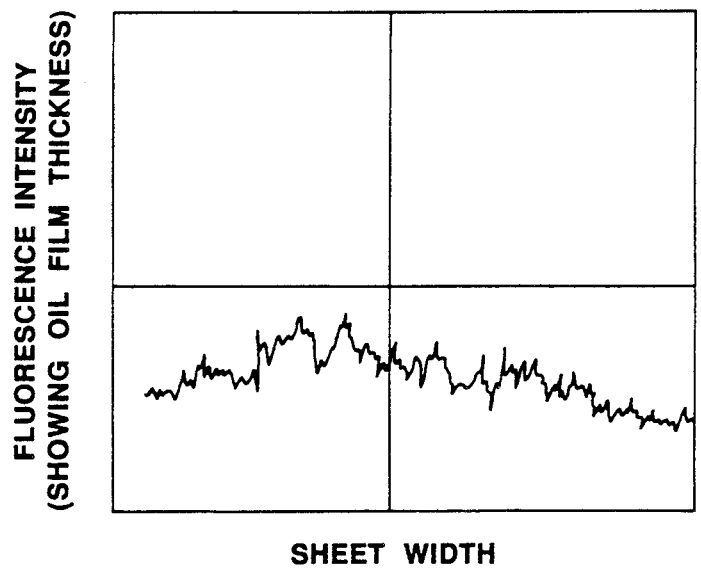

Other conditions were as follows.
Ultraviolet ray wavelength for excitation: 365 nm
Ultraviolet ray intensity for excitation: about 1500 $\mu W/cm^2$
Condition of image processing: Number of integrated images 64 frame background correction The output displays obtained by the above-mentioned procedures are shown in FIG. 6 to 8. FIG. 6 is the chart showing conditions obtained with no oil coating. FIG. 7 is the chart showing conditions obtained with 200 $mg/m^2$ of oil, and FIG. 8 is the chart showing conditions obtained with 400 $mg/m^2$ of oil.

Figure 9:
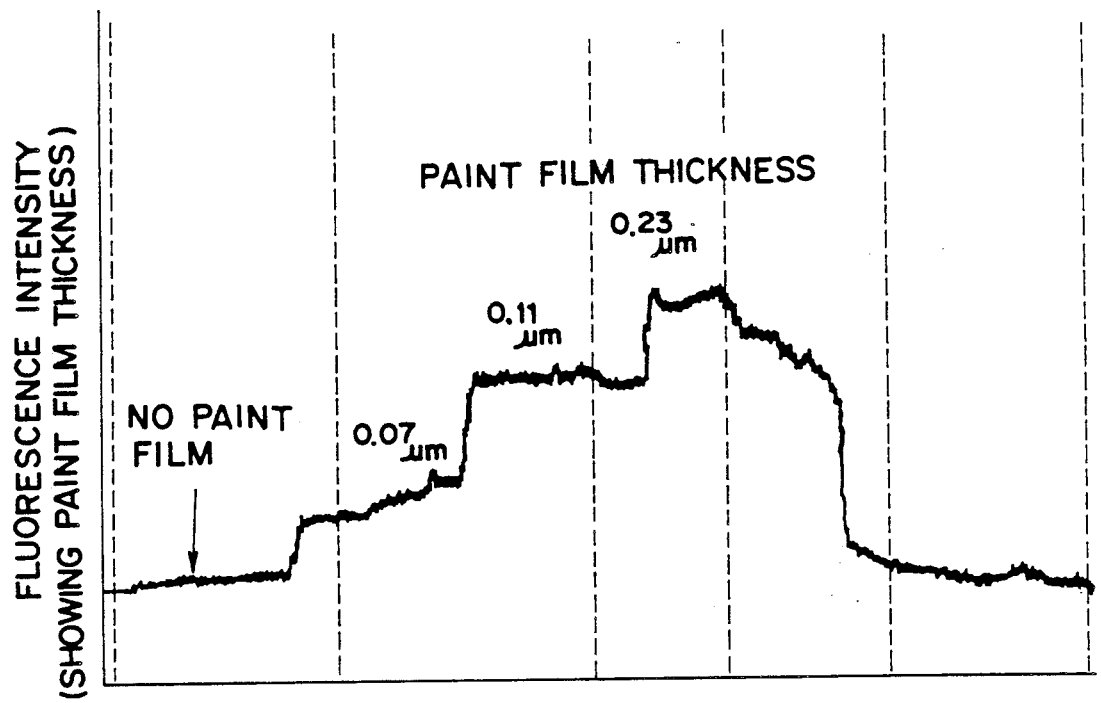
FIG. 9 shows the display of a signal output obtained with no paint coating, and obtained when 0.07 $\mu$m, 0.11 $\mu$m and 0.23 $\mu$m of paint film thickness.

On the same conditions, as mentioned above, the paint film coated on running aluminum sheets was also measured before and after painting. The output displays obtained by the procedures are shown in FIG. 9.

As mentioned above, adopting the measuring method and apparatus of this invention permits transformation of oil film inspection from the conventional off-line measurement to an on-line measurement system which can cover the entire surface of running sheet with high precision. Accordingly, application of this invention to processes such as the inspection control of reoiling or painting on aluminum sheets for can material will result in remarkable improvement of efficiency.

In addition to measuring the thickness of oil film or paint film, this invention can be used to detect the presence of oil or paint itself.

We claim:

1. An apparatus to measure the thickness of a coating film formed on a running metal sheet to which the coating film is applied, comprising: an ultraviolet radiation lamp to direct ultraviolet rays along a first axis onto the above-mentioned coating film; a high sensitivity TV camera to detect fluorescent light emitted from the coating film due to ultraviolet radiation, the high-sensitivity camera being set to receive fluorescent light traveling approximately parallel to a second axis oriented at an angle of 90° or less to the first axis of the ultraviolet radiation, the camera detecting fluorescent light emitted from the coating film across a full width of the metal sheet; an image processing device connected to the high-sensitivity TV camera and equipped with an integration circuit unit to amplify the signal intensity of the fluorescence detected by the high sensitivity TV camera, a linearizing unit to correct the linear relation between the intensity of the fluorescence and the coating thickness, and a background noise reducing unit to eliminate the distributive influence of ultraviolet ray radiation; and a display device which visually depicts the thickness of the coating film across the full width of the metal sheet and which is coupled to the image processing device.

2. An apparatus to measure the thickness of a coating film, as stated in claim 1, including a spectroscope which adjusts the ultraviolet radiation striking the oil film so that it has a wavelength within a range of 200 to 400 nm, the spectroscope being disposed in front of the ultraviolet radiation lamp.

3. An apparatus to measure the thickness of a coating film, as stated in claim 1, wherein said coating film is oil.

4. An apparatus to measure the thickness of a coating film, as stated in claim 1, wherein said coating film is paint.

5. An apparatus to measure the thickness of a coating film, as stated in claim 1, wherein the first axis and the second axis are substantially coincident, the angle therebetween being substantially 0°.

6. An apparatus to measure the thickness of a coating film, as stated in claim 1, including controller means for controlling the orientation of the TV camera.

7. An apparatus to measure the thickness of a coating film, as stated in claim 1, including a darkroom, the metal sheet having the coating film thereon traveling through the darkroom, and the ultraviolet radiation lamp and the TV camera being disposed within the darkroom.

* * * * *